(12) United States Patent
Yusibov

(10) Patent No.: US 7,012,172 B2
(45) Date of Patent: Mar. 14, 2006

(54) VIRUS INDUCED GENE SILENCING IN PLANTS

(75) Inventor: Vidadi Yusibov, Havertown, PA (US)

(73) Assignee: Fraunhofer, USA, Inc., Plymouth, MI (US)

( * ) Notice: Subject to any disclaimer, the term of this patent is extended or adjusted under 35 U.S.C. 154(b) by 324 days.

(21) Appl. No.: 10/205,562

(22) Filed: Jul. 25, 2002

(65) Prior Publication Data

US 2004/0019930 A1    Jan. 29, 2004

(51) Int. Cl.
  *C12N 15/82*    (2006.01)
  *C12N 15/83*    (2006.01)
(52) U.S. Cl. ...................................... 800/285; 800/280
(58) Field of Classification Search ............... 800/278, 800/279, 280, 285, 286, 288
  See application file for complete search history.

(56) References Cited

OTHER PUBLICATIONS

Kiyosue et al., Plant J., 2000, vol. 23, pp. 807-815.*
Thomas et al., Plant J., 2001, vol. 25, pp. 417-425.*
Angell et al., EMBO J., 1997, vol. 16, pp. 3675-3684.*

* cited by examiner

*Primary Examiner*—Ashwin Mehta
(74) *Attorney, Agent, or Firm*—Choate, Hall & Stewart, LLP

(57) ABSTRACT

The present invention discloses methods for interfering with expression of the genes in plant cells by using replicating recombinant viral vectors. A host plant is infected at one or more locations with a recombinant viral vector. The vector is both an initiator and a target of the RNA-triggered gene silencing in plant cells. The vector upon infection is capable of directing self-replication and producing a transcription product of a nucleic acid segment. The transcription product interferes with the expression of a specific gene in plant cells.

27 Claims, 9 Drawing Sheets

VIRUS INDUCED GENE SILENCING IN PLANTS

FIELD OF THE INVENTION

Figure 1:
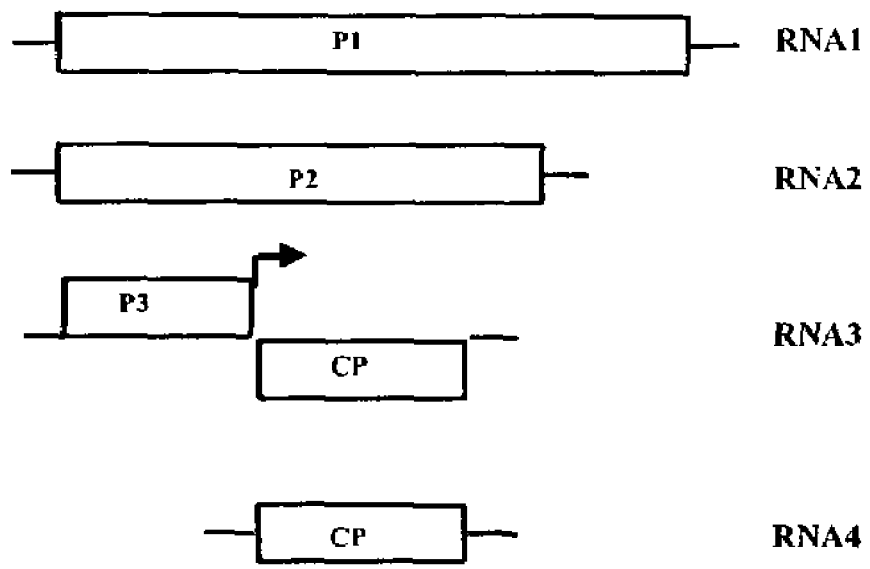

The present invention is in the field of functional genomics in plants and it involves the use of recombinant plant viral vectors. In particular, the present invention relates to methods for interfering with the expression of genes in plant cells and accumulation of recombinant viral vectors in these cells through RNA-triggered gene silencing.

BACKGROUND OF THE INVENTION

In recent years, as part of genome projects, the genomes of number of species of plants and animals have been completely sequenced. The ultimate goal of these genome projects is to identify the biological function of every gene in the genome. The functions of some of the genes have already been identified by various approaches. One approach to functional studies of gene/s is to knockout expression of target gene and monitor the effects of silencing phenotypically as well as biochemically. This is being carried out by using insertional mutagenesis, either by T-DNA or transposable elements, to knockout expression of target gene in transgenic plants. In addition to the insertional mutagenesis, overexpression of proteins is also being used to study function of genes. However, there are some drawbacks to each approach. Insertional mutagenesis results in complete inactivation of target gene, which may complicate the studies of embryo specific genes, especially if the gene is crucial for embryo development. Another point for concern is study of the gene in multi-gene family, where function of mutant gene could be compensated. In recent years, an alternative method for gene silencing to study gene function, virus induced gene silencing (VIGS), has emerged. This process facilitates targeted post-transcriptional gene silencing (PTGS). The host cell gene is being actively transcribed but no RNA accumulates or accumulates at levels lower than normal levels. This method combines new developments in virus-based expression vectors and discoveries in gene silencing. Segment(s) of host gene(s) are amplified in cells through infection with virus vectors capable of replication in plant cells. The presence of these aberrant or overexpressed RNA segments in cells results in the degradation of host mRNA containing the same sequence. It is reported that VIGS is caused by double stranded RNA formation through an RNA mediated defense mechanism. VIGS often results in a special phenotype, indicative of gene silencing. For example, inactivation of cellulose synthase gene resulted in much shorter internode length, small leaves, and a "dwarf" phenotype. Expression of mRNA fragments from phytoene desaturase using tobacco mosaic virus and potato virus X resulted in the discoloration of upper leaves of infected plant. See, U.S. Pat. No. 6,376,752. The cause of discoloration is a decline in the levels phytoene desaturase mRNA leading to lower levels of protein accumulation.

However, these prior art methods of VIGS involve the use of only mono-partite (single component) plant viral vectors with a limited host range. Further, these vectors are not capable of only local spread without systemic movement. Therefore, there is a need for developing methods involving the use of viral vectors that have a wider host-range and/or are incapable of systemic movement Further, the prior art vectors have been used for silencing of only one gene at a time. Given the number of genes whose function is not yet understood, vectors that can induce multiple gene silencing would be desirable, particularly for studies on metabolic pathways.

SUMMARY OF THE INVENTION

The present invention relates generally to methods for interfering with the expression of genes in plant cells and accumulation of recombinant plant viral vectors in these cells both of which are induced by the vectors. The recombinant plant viral vector can be derived from a genomic component of a plant virus that can be of a mono-, bi-, tri-partite genomic virus. Some of the vectors are incapable of systemic movement and some are capable of silencing multiple genes. The present invention also discloses methods for silencing genes in a transgenic host plant.

Specifically, in one aspect of the invention, a method for interfering with the expression of a selected gene in plant cells through RNA-triggered gene silencing initiated by a recombinant viral vector is provided. In this method, plant cells are infected at one or more locations of a host plant with the recombinant viral vector. The viral vector is derived from a recombinant genomic component of a plant virus. The recombinant genomic component of the plant virus has a nucleic acid segment of the selected gene (heterologous to the viral genome). The vector, upon infection, is capable of directing self-replication and producing a transcription product of the nucleic acid segment in said cells but incapable of systemic movement in the host plant. The nucleic acid segment is expressed from a subgenomic promoter of the plant virus coat protein gene or movement protein gene and is expressed as part of messenger RNA (mRNA) of the coat protein gene or movement protein gene. Then the host plant is grown for sometime. The transcription product interferes with the expression of the selected gene in the plant cells. The interference can be determined by a genetic, biochemical or phenotypic changes. These are attributable to the interference. The nucleic acid segment does not occur as such or at the same location in the genome of the plant virus (wildtype virus). The nucleic acid segment consists of at least about 20 nucleotides and consists of up to 200 nucleotides or up to 300 nucleotides. The selected gene is native to the host plant or a transgene in the host plant. The transgene can be for example, the plant virus replicase gene or a crown gall gene or the transgene is native to a monocotyledonous or dicotyledonous plant. The subgenomic promoter is not of the coat protein gene or the movement protein gene but a synthetic or artificial or heterologous subgenomic promoter. The nucleic acid segment may be expressed under a separate promoter independently of viral genes, for example, P3 or CP.

In another aspect of the invention, a method for interfering with expression of a selected gene in plant cells through RNA-triggered gene silencing is provided. It involves, first, infecting said cells at one or more locations of a host plant with a recombinant viral vector which is both an initiator and a target of the RNA-triggered gene silencing in said cells. The vector has a recombinant genomic component of a plant virus and a nucleic acid segment of the selected gene. The vector, upon infection, is capable of directing self-replication and producing a transcription product of the nucleic acid segment in the cells but incapable of systemic movement in the host plant. The nucleic acid segment is expressed from a subgenomic promoter of the plant virus coat protein gene or movement protein gene and is expressed as part of messenger RNA (mRNA) of the coat protein gene or movement protein gene. Then, the host plant is grown. The transcription product interferes with the expression of the selected gene in the cells as determined by a genetic, biochemical or phenotypic change attributable to said interference.

In still another aspect of the invention, a method for interfering with the expression of a selected gene in plant cells and accumulation of a recombinant viral vector in said cells through RNA-triggered gene silencing is provided. It involves, infecting the cells of a host plant at one or more locations with the recombinant viral vector which is both an initiator and a target of the RNA-triggered gene silencing in the host plant. The viral vector may have a recombinant genomic component of a plant virus and a nucleic acid segment of the selected gene. The viral vector, upon infection, is capable of directing self-replication and producing a transcription product of the nucleic acid segment at said locations but incapable of systemic movement in the host plant. The nucleic acid segment is expressed from a subgenomic promoter of the plant virus coat protein gene or movement protein gene and is expressed as part of messenger RNA (mRNA) of the coat protein gene or movement protein gene. Then, the host plant is grown for sometime. The transcription product interferes with the expression of the selected gene in the cells as determined by a genetic, biochemical or phenotypic change attributable to the interference, and the accumulation of the recombinant viral vector.

In yet another aspect of the invention, a method for interfering with the expression of selected genes in plant cells of a host plant through recombinant viral vector initiated RNA-triggered gene silencing is provided. In this method cells are infected at one or more locations of the host plant with at least two types of recombinant viral vectors such that each of the vectors, upon infection, is capable of directing self-replication and producing a transcription product of a nucleic acid segment present in each of the vectors at those infected locations, which nucleic acid segment is also found in one of the plant expressed genes. The nucleic acid segment is expressed from subgenomic promoter of the plant virus coat protein gene or movement protein gene and is expressed as part of messenger RNA (mRNA) of the coat protein gene or movement protein gene. The first type of recombinant viral vector has a recombinant genomic component of a plant virus, and a nucleic acid segment of a first gene. The second type of recombinant viral vector has the recombinant genomic component of the plant virus, and a nucleic acid segment of a second gene. The vectors are both initiators and targets of the RNA-triggered gene silencing in the host plant. Then the host plant is grown for some time. The transcription product interferes with the expression of the selected gene in the cells as determined by a genetic, biochemical or phenotypic change attributable to the interference. The vectors can be so constructed that the vectors are capable of limited cell-to-cell movement but incapable of systemic movement in the host plant. The first and second vectors can be administered either simultaneously or sequentially at the same location or at different locations of the host plant.

In yet another aspect of the invention, a method for interfering with the expression of selected genes in plant cells of a host plant through recombinant viral vector initiated RNA-triggered gene silencing is provided. In this method, the host plant cells are infected at one or more locations with a first recombinant viral vector and a second recombinant viral vector so that each of the vectors, upon infection, is capable of directing self-replication and producing a transcription product of a nucleic acid segment present in each of the vectors at said locations, which nucleic acid segment is also found in one of the plant expressed genes. The first recombinant viral vector has a recombinant genomic component of a first class of plant virus and a nucleic acid segment of a first gene such that the nucleic acid segment of the first gene is expressed from subgenomic promoter of the first class of plant virus coat protein gene or movement protein gene and is expressed as part of messenger RNA (mRNA) of the coat protein gene or movement protein gene of the first class of virus. The second recombinant viral vector has a recombinant genomic component of a second class of plant virus and a nucleic acid segment of a second gene such that the nucleic acid segment of the second gene is expressed from subgenomic promoter of the second class of plant virus coat protein gene or movement protein gene and is expressed as part of messenger RNA (mRNA) of the coat protein gene or movement protein gene of the second class of virus. The vectors are both initiators and targets of the RNA-triggered gene silencing in the host plant. When the host plant is grown for some time, the transcription product interferes with the expression of each of said genes in said cells as determined by a genetic, biochemical or phenotypic change attributable to the interference.

In another aspect of the invention, a method for interfering with expression of selected genes in plant cells through recombinant viral vector initiated RNA-triggered gene silencing, is provided. Plant cells are infected at one or more locations of a host plant with a first and second recombinant viral vectors. The first vector has a recombinant genomic component of a first class of plant virus and a nucleic acid segment of a first gene such that the nucleic acid segment of the first gene is expressed from subgenomic promoter of the first class of plant virus coat protein gene or movement protein gene and is expressed as part of messenger RNA (mRNA) of the coat protein gene or movement protein gene of the first class of virus. The second recombinant viral vector, has a recombinant genomic component of a second class of plant virus and a nucleic acid segment of a second gene such that the nucleic acid segment of the second gene is expressed from subgenomic promoter of the second class of plant virus coat protein gene or movement protein gene and is expressed as part of messenger RNA (mRNA) of the coat protein gene or movement protein gene of the second class of virus. The vectors are both initiators and targets of the RNA-triggered gene silencing in the host plant. The vectors, upon infection, are capable of directing self-replication and producing a transcription product of the nucleic acid segment present in each of the vectors. At least one of the vectors is capable of systemic movement in the host plant. By growing the host plant for some time, the transcription product interferes with the expression of each of the genes in the cells as determined by a genetic, biochemical or phenotypic change attributable to the interference.

In yet another aspect of the invention, a method for interfering with the expression of a selected gene in plant cells through RNA-triggered gene silencing is provided. It involves infecting the cells at one or more locations of a host plant with a recombinant viral vector, the vector has a recombinant genomic component of AlMV and a nucleic acid segment of the selected gene. The vector, upon infection, is capable of directing self-replication and producing a transcription product of the nucleic acid segment. The nucleic acid segment is expressed from subgenomic promoter of the AlMV coat protein gene or movement protein gene and is expressed as part of messenger RNA (mRNA) of the coat protein gene or movement protein gene and the vector is both an initiator and a target of the RNA-triggered gene silencing in the cells. By growing the host plant, the transcription product interferes with the expression of the selected gene in the cells as determined by a genetic, biochemical or phenotypic change attributable to the interference. The recombinant genomic component of AlMV has replicase nucleic acids, a movement protein encoding nucleic acid sequence and a coat protein encoding nucleic acid sequence lacking one or more nucleotides sufficient to prevent translation of coat protein.

In another aspect of the invention, a method for interfering with the expression of selected genes in plant cells through RNA-triggered gene silencing is provided. It involves infecting the cells at one or more locations of a host plant with a recombinant viral vector. The vector has a recombinant genomic component of a plant virus, a nucleic acid segment of a first gene placed immediately upstream of movement protein nucleic acid sequence in the genomic component of AlMV and under control of a subgenomic promoter also controlling the movement protein sequence a nucleic acid segment of a second gene placed immediately upstream of coat protein nucleic acid sequence in the genomic component of the plant virus and under control of a subgenomic promoter also controlling the coat protein sequence. The vector, upon infection, is capable of directing self-replication and producing a transcription product of the nucleic acid segments. The vector is both an initiator and a target of the RNA-triggered gene silencing in the cells. The host plant is grown for some time. The transcription product interferes with the expression of the first or the second gene in the cells as determined by a genetic, biochemical or phenotypic change attributable to the interference. The plant virus can be TMV or AlMV.

BRIEF DESCRIPTION OF THE DRAWINGS

FIG. 1. Schematic representation of genome of AlMV.

FIG. 2. Schematic representation of strategies for engineering of recombinant viral vectors based on AlMV and TMV genomes for gene silencing.

FIG. 3. Schematic representation of VMB-RBC (Rubisco) (SEQ ID NO. 10) and VMB-bAS (beta-amyrin synthase) (SEQ ID NO. 11) engineered using AlMV RNA3.

FIGS. 4A and 4B. Schematic representation of various vector designs for multiple gene silencing.

FIG. 5. Western blot analysis of CP in plants infected with wt AlMV or NF1-P1.

FIG. 6. Western analysis of alfalfa mosaic virus coat protein accumulation in cotyledons (cot), leaves (l) and roots (r) of *Medicago truncatula* 10 dpi (days post inoculation).

FIG. 7. Western analysis of alfalfa mosaic virus coat protein accumulation in cotyledons (7 dpi) and systemically infected leaves (14 dpi) of *Medicago truncatula.*

FIG. 8. Photographs of *Medicago truncatula* showing phenotypic changes attributable to interference with Rubisco. (All plants shown were infected with a viral vector for VIGS.)

FIG. 9. Photographs of *Nicotiana benthamiana* showing phenotypic changes attributable to interference with Rubisco. (The plant on the right is infected with a viral vector for VIGS. The plant on the left is a control plant.)

DETAILED DESCRIPTION OF THE INVENTION

The present invention relates to gene silencing and provides tools and methods to selectively interfere with gene expression or function. Gene silencing can occur at either the transcriptional or posttranscriptional level. The present disclosure deals with methods for interfering with expression of selected gene(s) in plant cells through RNA-mediated gene silencing (RNA silencing). As is known to one skilled in the art, RNA silencing refers to a group of interrelated, sequence specific, RNA-targeted gene silencing mechanism. In particular, the methods of the invention permit the assignment of function to a gene expressed by plant cells through RNA silencing. The silencing involves a nucleotide sequence-specific RNA degradation. The present invention employs plant RNA virus based viral vectors to induce the nucleotide sequence-specific degradation of cellular RNAs in the host plant cells. The vector can also be a victim of the RNA silencing. Thus, the viral vectors used herein for gene silencing in plants can be both initiators and targets of the gene silencing.

By using the methods disclosed herein, interference with the expression of 3 different genes in plant cells has been done. These are AlMV replicase gene (P1) in transgenic P12 plants of tobacco, Ribulose bisphosphate carboxylase (Rubisco) in *Medicago truncatula* and *N. benthamiana* plants (See Examples 1 and 2) and beta-amyrin synthase gene (data not presented).

Accordingly, disclosed herein are recombinant viral vectors based on plant RNA viruses. The vectors are designed such that these vectors, upon infection, are capable of replicating in the host cell. The movement of the viral vector in the host plant is either limited to local spread without the ability to spread systemically or is capable of systemic spread. Systemic infection or the ability to spread systemically of a virus is the ability of the virus to spread from cell to cell and to replicate and express throughout the plant or in most of the cells of the plant. Each of these vectors carry a nucleic acid segment that corresponds to either fully or to a portion of a specific plant expressed cellular mRNA that is of interest for silencing. In other words, the specificity of the silencing would be accomplished by simply inserting a single copy of target gene (selected gene) sequence into the viral vector such that the sequences in the replicating vectors target specific transcripts for destruction. The nucleic acid segment in the vector is thus a heterologous nucleic acid sequence or the one that is not naturally present in the virus at the inserted location. The inserted nucleic acid segment can be several nucleotides long depending on the selected gene and the viral vector. For example the segment can be 20 nucleotides to 300 nucleotides long. In most cases, for example, a fragment of up to 200 nucleotides long can be used. Delivery of the nucleic acid segment into plant cells and its amplification therein by the vectors of the invention result in inhibition or decreased expression of the target gene.

The selected gene is an endogenously expressed gene which can be either a gene native to the host plant (e.g., Rubisco) or a transgene (e.g., viral replicase gene or a crown gall gene) in the host plant (e.g. Tobacco or Alfafa). The target genes of a host plant can be selected from a set of unique sequences (e.g., open reading frames or ORFs) from a given database. There are a number of sequence databases for plants that are known in the art. For example, sequence databases are available for *Arabidopsis,* rice, *Medicago,* soybeans, etc. There are a number of tools known to one skilled in the art that allow the rapid identification and screening of open reading frames (ORFs) in a DNA sequence. From the ORF of each target gene, one can select a segment of 100–200 nucleotides or longer region. PCR can be used for amplification of the desired fragment to be cloned into a viral vector. The fragment is cloned into a virus vector in sense/antisense orientation and the vector is used to inoculate a host plant (e.g., *M. truncatula* plants). Further, one skilled in the art would know the orientation of the segment to be inserted into the vector. The PCR products can be cloned directly into the viral vector by single step cloning. For one step cloning, the following strategy may be used. First, target sequences are selected from a target gene. Then, primers are designed and synthesized. Desired restriction sites (also present in the multiple cloning sites in the vector) are incorporated into 5' and 3' primers for cloning target sequences into the viral vector. PCR is performed. PCR products are digested with the same restriction enzymes for which sites were introduced during PCR of the target sequences. Digested PCR products are ligated into the vector. Sequence confirmation may be done before constructs can be used to study functional activity of the target gene.

Table 1 provides a list of examples of nucleic acid segments of various genes and the primers to clone such segments into the recombinant plant viral vectors of the invention.

It is known in the art that RNA viruses replicate their genomes through complementary RNA strands. The viral replication precedes the interference with the expression of a selected gene in plant cells. The process of interference with the gene expression or RNA silencing inside the plant cell may begin as the quantity of RNA from the replicating vectors begin to build up. For example, it can begin as early as 7 days after inoculation of the plant with the vector and severe RNA silencing can be observed by 14 days post infection (see examples below). It can be The interference by the viral vectors of the invention can be determined by phenotypic changes in the infected plant as compared to the control uninfected plants or those infected with vectors not capable of inducing the gene silencing. Phenotypic changes as used herein refer to visual or morphological changes. Alternatively, or in addition to the phenotypic changes, the interference can be determined by analyzing the mRNA or protein of the selected gene expressed by the plant cells. Accordingly, one skilled in the art would comprehend that the assignment of gene function can be done after taking into account of the specific phenotype or other changes resulting directly or indirectly from the interference through RNA silencing in the host plant infected with the viral vectors of the present invention.

Figure 8:
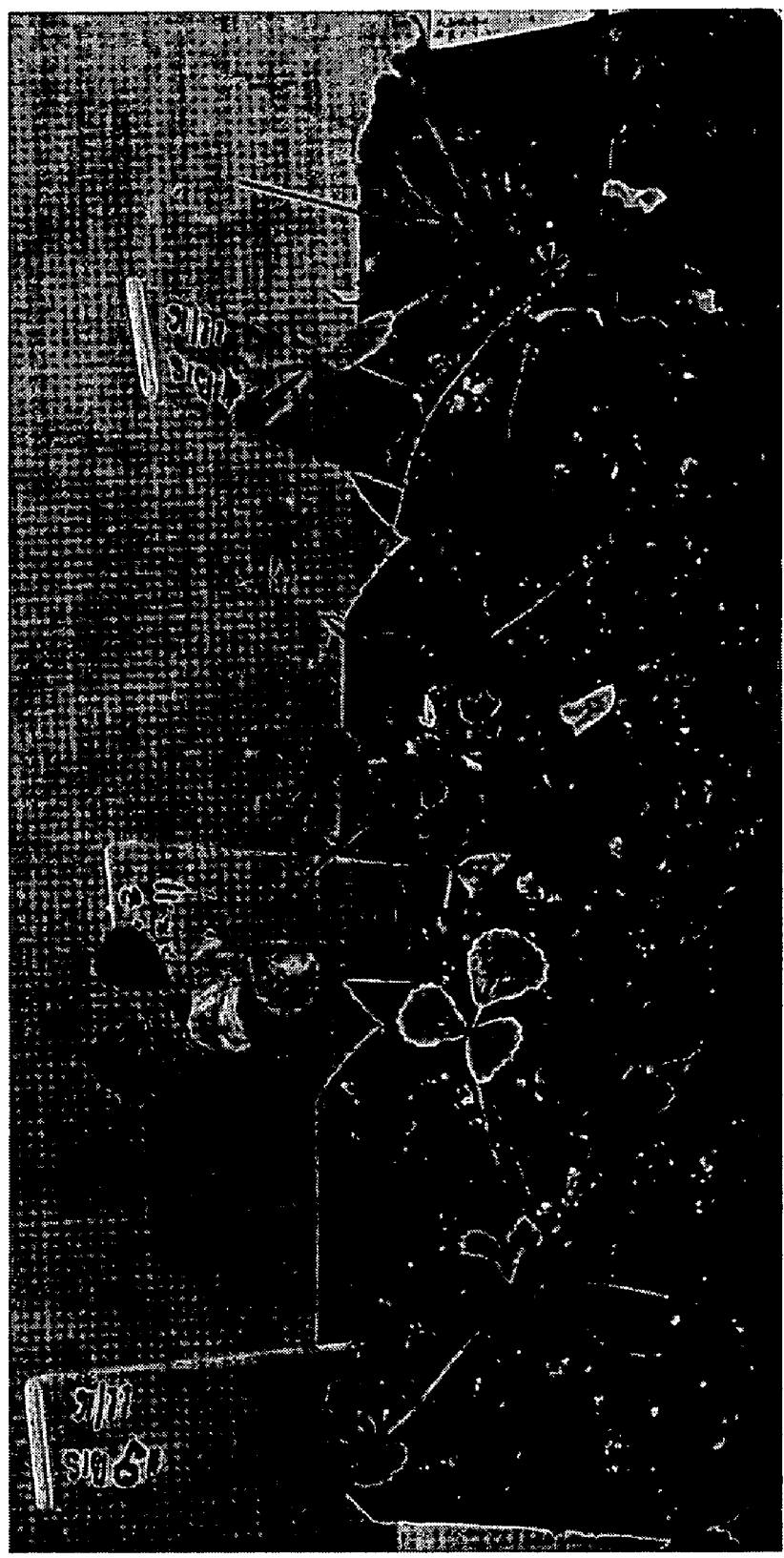
Figure 9:

In FIG. 8, photographs of *Medicago truncatula* infected with a viral vector for Rubisco silencing are shown. These plants show chlorosis, small leaves and bushy growth as compared to the controls which are not shown here. Photographs of *Nicotiana benthamiana* showing phenotypic changes attributable to interference with Rubisco are shown in FIG. 9. The plant on the right is infected with a viral vector for VIGS. This plant shows small curly leaves as opposed to the plant on the left which is a control plant.

The selected genes expressed by the plant cells can be, for example, a lignin specific gene, a phloem specific gene, a flavonoid pathway gene, a receptor gene, a hormonal gene, a gene specific to fruit maturation, a gene responsible for fatty acid synthesis, a gene responsible for starch or cellulose synthesis, a gene specific to seed maturation, a gene specific to seed germination, a gene responsible for enhanced root formation, a gene responsible for tissue regeneration in vitro, a gene responsible for tissue for transport protein, a gene responsible for signal transduction, a crown gall gene, beta-amyrin synthase gene, Rubisco gene or chalcone synthase gene by a genetic, biochemical or phenotypic change attributable to said interference.

A recombinant viral vector for carrying out the methods of the invention can be constructed by manipulating the genomic component of a plant virus particularly an RNA virus. The plant viruses can be mono-, bi- or tri-partite viruses and such viruses are well known to one skilled in the art. "Genome" refers to the total genetic material of the virus.

These viruses include Alfalfa Mosaic Virus (AlMV), ilarviruses, cucumoviruses such as Cucumber Green Mottle Mosaic virus (CGMMV), closteroviruses or tobamaviruses (tobacco mosaic virus group) such as Tobacco Mosaic virus (TMV), Tobacco Etch Virus (TEV), Cowpea Mosaic virus (CMV), and viruses from the brome mosaic virus group such as Brome Mosaic virus (BMV), broad bean mottle virus and cowpea chlorotic mottle virus. Additional suitable viruses include Rice Necrosis virus (RNV), and geminiviruses such as tomato golden mosaic virus (TGMV), Cassaya latent virus (CLV) and maize streak virus (MSV). Each of these groups of suitable viruses are well characterized and are well known to the skilled artisans in the field.

The vectors used in the present invention can be in DNA or RNA form. Preferred viral vectors are those derived from the genomes of AlMV and TMV. These vectors (AlMV and TMV) have been used by those skilled in the art to produce polypeptides in plants. See, U.S. Pat. No. 6,042,832; WO 96/12028; WO 00/25574. In a particularly preferred embodiment of the invention, alfalfa mosaic virus (AlMV) is used to make a vector for VIGS. This vector can accommodate significant size fragments (e.g., 300 nucleotides) from a given gene (the target gene). AlMV is a positive sense RNA virus (tri-partite virus) with the genome consisting of three genomic RNAs and subgenomic RNA4. AlMV virions are encapsidated by a unique coat protein (24 kD) and form particles that differ in size (30- to 60-nm in length and 18 nm in diameter) and form (spherical, ellipsoid or bacilliform) depending on the size of the encapsidated RNA. In addition, AlMV has a wide host range, including *M. truncatula* (as shown below).

FIG. 1 shows genome of AlMV. The arrow (→) in RNA3 in FIG. 1 and in other Figures indicates subgenomic promoter. As to the vector preparation of AlMV, purified plasmid DNAs corresponding to genomic RNAs 1, 2 (pUT17 and pUT27, respectively), 3 (recRNA3), or subgenomic RNA4 (pSP65A4) of AlMV is linearized with SmaI at the 3' end of the viral RNA sequences before in vitro transcription reactions. In one preferred embodiment, a region of target gene is cloned into RNA3 and expressed in plants as part of subgenomic RNA4 as well as genomic RNA3.

The vectors may have the transcription termination regions. The transcription termination region is a sequence that controls formation of the 3' end of the transcript, e.g., polyadenylation sequences and self-cleaving ribozymes. Termination signals for expression in other organisms are well known in the literature. Sequences for accurate splicing of the transcript may also be included. Examples are introns and transposons.

Figure 2:
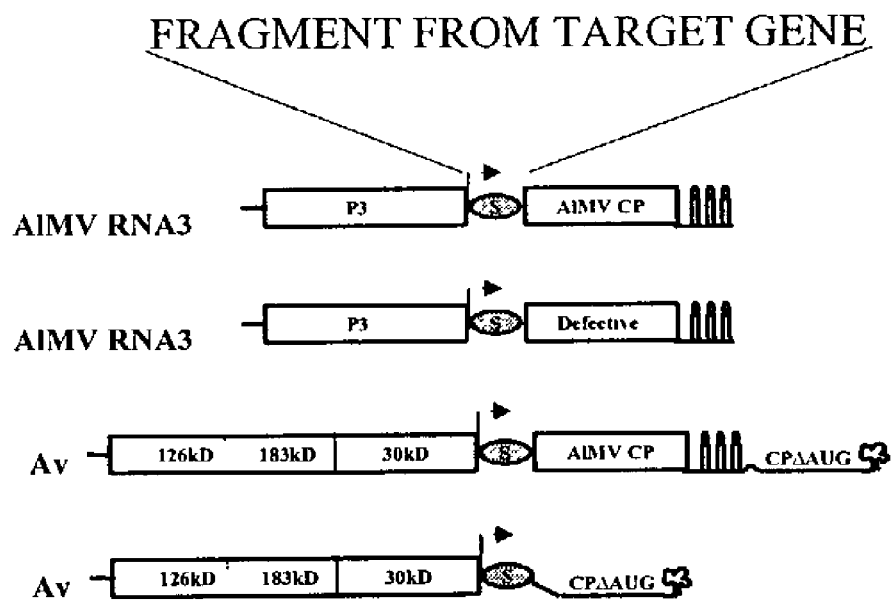
Figure 3:
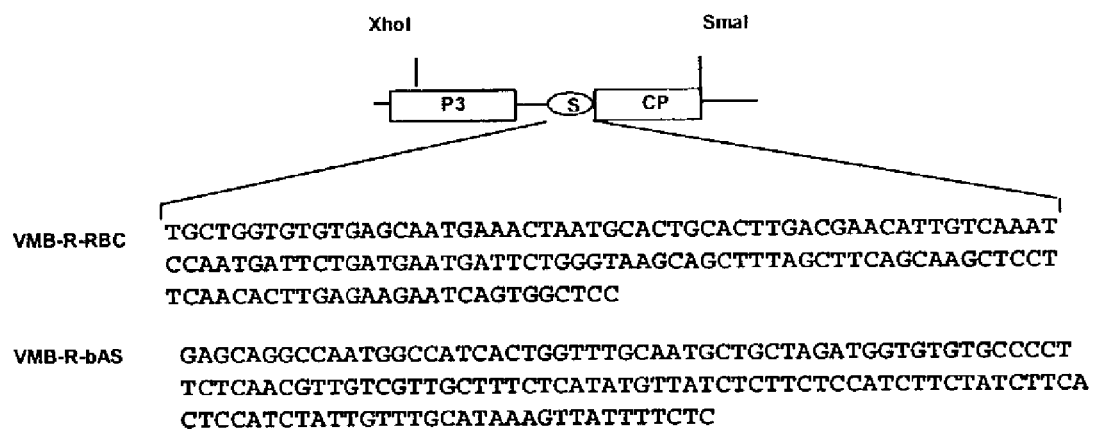
Figure 4:
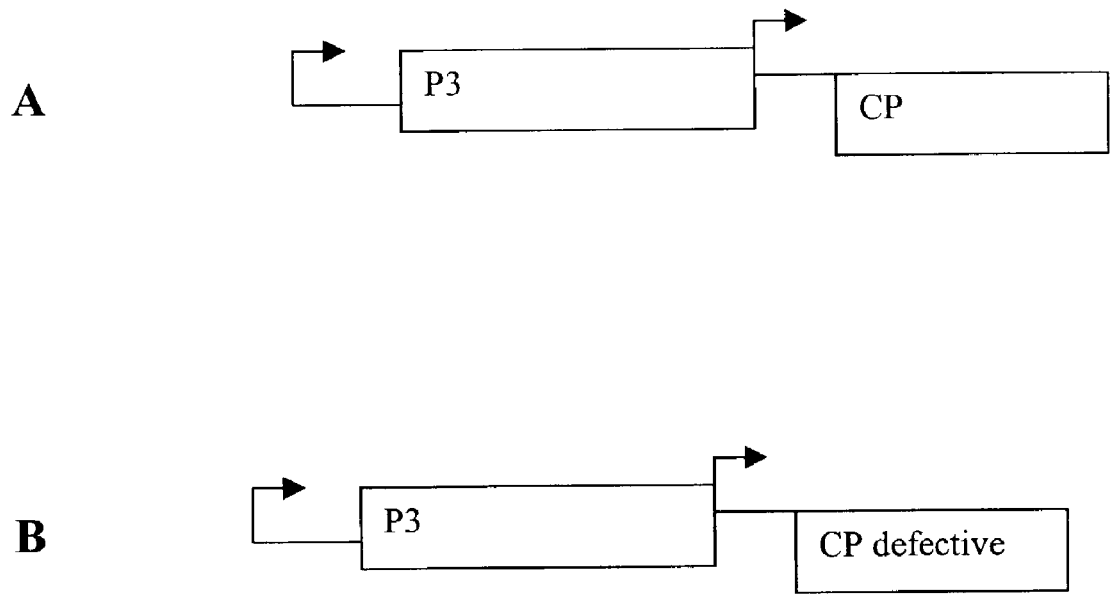

Shown in FIG. 2 are schematic representations of different AlMV (2A and 2B) and TMV (2C and 2D) based vectors for VIGS. Of these, the vectors shown in FIGS. 2A and 2C are for systemic infection and those shown in FIGS. 2B and 2D are for local infection. The letter "s" stands for a nucleic segment of the plant expressed gene. For example the segment can be that of Rubisco gene or beta-amyrin synthase gene. See FIG. 3.

Recombinant viral vectors used herein can be in vitro transcripts, or DNA constructs. In vitro transcripts can be prepared as follows. After assembly of a recombinant genomic component and heterologous nucleic acid sequence(s), this combination can be placed behind (downstream of) a heterologous promoter that can drive in vitro transcription of the downstream sequences to produce in vitro transcripts. Examples of efficient heterologous promoters for in vitro transcription include a bacteriophage promoter such as the T7 phage promoter or 5P6 promoter. After such a viral vector/in vitro transcription vector combination is assembled, in vitro transcripts for infection can be produced by in vitro transcription and mixed with any other viral RNA in vitro transcripts necessary for maintenance of the viral vector in a plant cell. RNA production from the vector can be conducted, for instance, with the method described in Yusibov et al., 1998, Virology, 242:1–5. For example, in vitro transcripts of AlMV RNAs can be synthesized using T7 (for genomic RNAs 1, 2, and 3) or P6 (for subgenomic RNA4) RNA polymerases (Promega, Madison, Wis.) and purified plasmid DNA, according to the manufacturer's guidelines. Reactions can be performed in 100 .mu.1 volume. Transcripts are capped using, for example, the RNA cap structure analog m7G(5)ppp(5)G (Biolabs, Beverly, Mass.).

The in vitro transcripts for infection can be applied to cell(s) of a plant by any of the techniques known to those skilled in the art. Suitable techniques include, but are not limited to, hand inoculations such as abrasive inoculations (leaf abrasion, abrasion in a buffer solution), mechanized spray inoculations, vacuum infiltration, particle bombardment and/or electroporation.

Mixture of in vitro transcription products containing infectious RNAs 1, 2, 3, and subgenomic RNA4 can be used to inoculate a host plant protoplasts (e.g., tobacco protoplasts) by electroporation. About 20 hours after electroporation, samples are collected and screened for virus infection. Aliquots of this sample can be used to inoculate host plants (e.g., M. truncatula seedlings). To generate wild type AlMV for use in control experiments a suitable plant (e.g., N. tabacum cv. Xanthi-nc plant) can be inoculated with AlMV particles diluted in FES buffer (2 ng/µl) onto 4 upper leaves (at 6-leaf stage). After inoculation, plants can be monitored for virus infection as well as gene silencing and visual effects of gene silencing.

Suitable buffer solutions in which the recombinant vectors are suspended to prepare inoculum for inoculation are well known in the art. For example, leaves of plants can be inoculated with in vitro transcription products of recombinant viral vectors (as described in Yusibov et. al., 1997) after adding 1 vol (v/v) of FES buffer [sodium-pyrophosphate 1% (w/v), malacoid 1% (w/v), celite 1% (w/v), glycine 0.5 M, $K_2HPO_4$ 0.3 M, pH 8.5, with phosphoric acid]. The mixture in vitro transcription products and FES buffer can be applied to leaves after abrading the leaf surface with carborundum (320 grit; Fisher, Pittsburgh, Pa.). Inoculation can be affected by gentle rubbing to spread the inoculum and further abrade the leaf surface.

Different types of vectors with different capacities in infection are contemplated. For example, suitable vectors can be designed for systemic infection. These vectors (as demonstrated in the Examples section below) can be highly effective in plant infection and silencing of target gene. The nucleic acid segment (for RNA silencing) cloned into the systemic vectors may be engineered to have a start codon (e.g., ATG) at the 3' end of the segment but not at the 5' end. Such a fragment when placed under the control of a subgenomic promoter is not itself translated but provides the start codon for the sequences immediately downstream of the segment so that these downstream sequences may be translated. The downstream sequences may be, for example, P3 or CP of AlMV without a start codon which may have been lost during the digestion of the vector and cloning of the nucleic acid segment into the vector. The vectors can also be engineered in a manner that initiation of target gene silencing also initiates destruction and elimination of the vector from plant (approximately 15–20 days after inoculation) to minimize potential interference with the viral infection symptoms (not related to the RNA silencing) that may follow silencing of a target gene. While AlMV (vector) persists in infected M. truncatula plants for more than five month resulting in significant stunting and symptom formation, the subject engineered target constructs are cleared within 2–3 weeks of inoculation. In these plants, no stunting and no residual symptoms of virus infection are seen.

Figure 6:
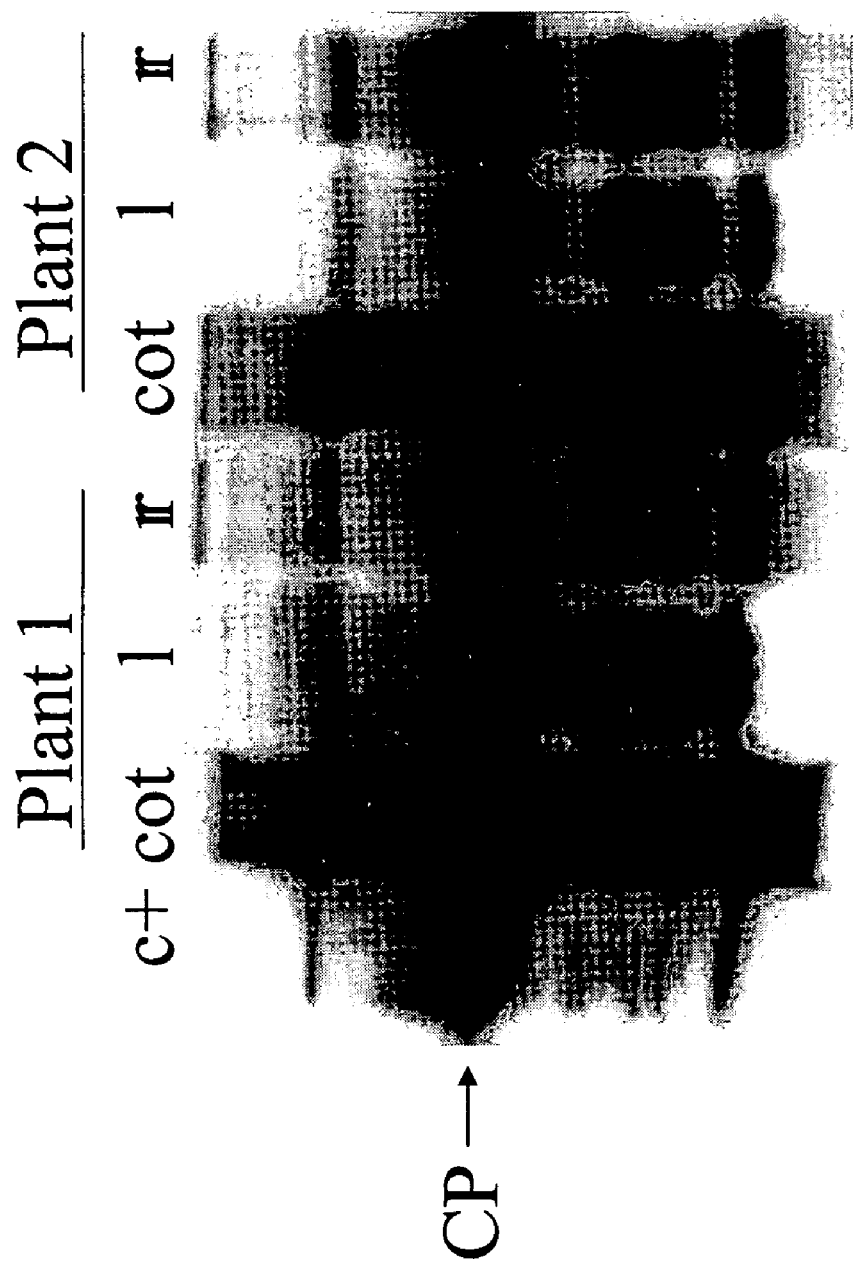
Figure 7:
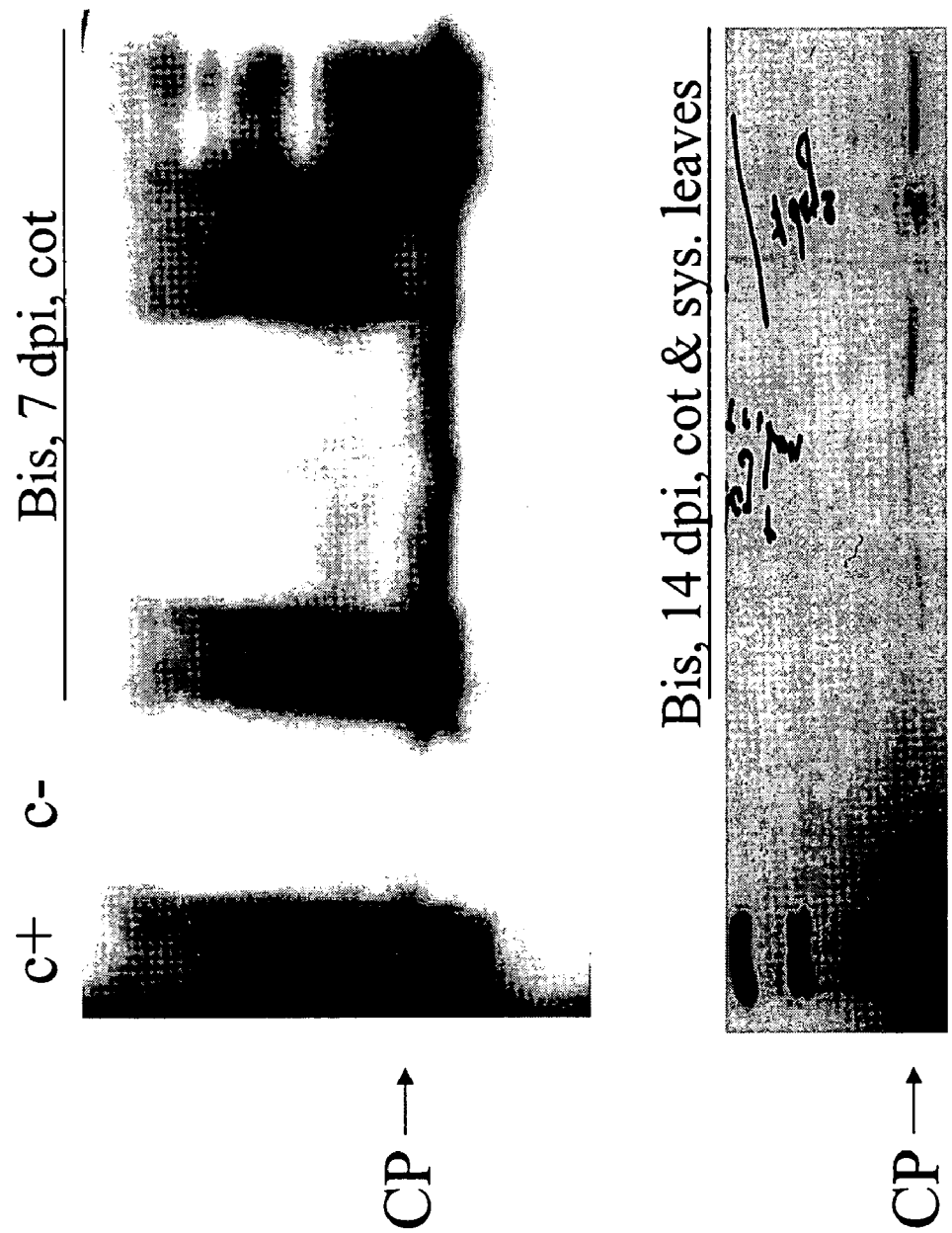

FIG. 6 shows accumulation of the viral vector in different organs of a host plant after inoculation with an AlMV viral vector capable of systemic spread. More specifically, the illustration shows western analysis of alfalfa mosaic virus coat protein accumulation in cotyledons (cot), leaves (l) and roots (r) of Medicago truncatula 10 dpi (days post inoculation). Presented in FIG. 7 is western analysis of alfalfa mosaic virus showing coat protein accumulation in cotyledons (7 dpi) and systemically infected leaves (14 dpi) of Medicago truncatula. By 14 dpi, the viral vector accumulation is significantly decreased.

Other suitable vectors can also be designed so that these can be used only for localized infection. These vectors (as demonstrated in the Examples section below) can be highly effective in plant infection and local spread only (e.g., confined to inoculated leaves only without the ability to move systemically). The plant viral vectors used in the present invention require the coat protein for their systemic movement. But local vectors are designed to be defective in coat protein production. This can be done by deleting portions of open reading frame including the start codon so that no translation of the coat protein RNA sequence takes place. However, the regulatory sequences, such as 5' and 3' non-coding regions, critical for replication and cell-to-cell movement have to be in place. For example: Av's based on TMV that is lacking CP and some of CP sequences: Such viral vectors remain local. To test vectors for their ability to remain local, and not spread systemically, absence of coat protein in the infected cells can be used as a marker. Alternatively, fluorescent markers can be used (e.g., Av and Av+GFP can be used as visible marker for silencing).

The local vectors, like systemic vectors, after replication in the plant cells for some period of time, cause interference not only with the gene expression but also with the vector accumulation (i.e., RNAs of both the vector and the gene are targeted). The infection does not spread beyond the borders of infected regions. For example, if a leaf is infected, the infection does not spread beyond this leaf.

It is known in the art that the viral coat protein gene is needed for genome activation and systemic infection. However, a full-length sequence is not needed for the genome activation and systemic infection. For example, it is known in the art that a number of amino acids (up to 12 amino acids) can be deleted from the N-terminus of the AlMV coat protein without altering its systemic function. Deletion of more than 14 amino acids of AlMV coat protein may abrogate its systemic function. Numerous methods are known to one skilled in the art to delete sequences from nucleic acid sequences. Accordingly, the invention also uses vectors with mutated or deleted versions of a coat protein nucleic acid sequence of viral genomic component such that the vector remains local. Deletion and modification approaches can also be applied to the other nucleic acid sequences of a virus such as the movement protein encoding sequences.

The present invention also allows suppression of more than one gene in the infected plant. In an embodiment this aspect of gene silencing, a vector of the present invention may carry a nucleic acid segment that corresponds to either fully or to a portion of specific plant expressed cellular mRNAs that are of interest for silencing. For example, the nucleic acid segment of 200 nucleotides may have stretches of 50 contiguous nucleotides each (based on sequences for 4 different plant expressed genes) and each of these stretches correspond either fully or to a portion of specific plant expressed cellular mRNAs. Thus, the nucleic acid segment is so constructed that it will have 4 subsegments of 50 contiguous nucleotides each. Each subsegment is meant for degradation of a specific mRNA and the replicating viral vector carrying such a nucleic acid segment can interfere with the expression of 4 different genes. Thus, these vectors can be used for multiple gene silencing.

In another embodiment of multiple gene silencing, a vector of the present invention may carry two nucleic acid segments that correspond to either fully or to a portion of specific plant expressed cellular mRNAs that are of interest for silencing. The two nucleic acid segments are inserted at different positions of the vector. Each of the two nucleic segments may carry subsegments for multiple gene silencing as described in the preceding paragraph. FIG. 4 shows schematics of vectors for interfering with expression of 2 different endogenous genes in a host plant. Target gene fragments can be inserted into genomic RNA3 at 2 positions under 2 subgenomic promoters (FIG. 4A). This type of vectors are referred to herein as vectors for double silencing. The nucleic acid segments are expressed as part of the genomic and subgenomic RNA (movement protein (P3) and coat protein (CP)) but not as part of the ORFs of the P3 and CP. This type of vector can be used for systemic infection. In FIG. 4B, target genes are inserted into genomic RNA3 at 2 positions under 2 subgenomic promoters but this vector has a disabled CP so that it cannot spread systemically. The subgenomic promoters can be native, heterologous or a synthetic promoter.

In all cases, whether local or systemic, the nucleic acid segments may be cloned to be part of genomic or subgenomic RNA. However these are not part of P3 or CP ORFs and the segments are not translated.

The vectors of the invention can be delivered at different growth stages such as seedling stage, leaf stage, flowering, seed formation and maturation stages through roots, cotyledons, leaves, seed coat, seeds, pods, stem inoculations, etc. The vector inoculum can be applied at one or more locations of a host plant. For example, the inoculum can be applied on leaves and roots either simultaneously or successively. Alternatively, the inoculum can be applied at the same location (e.g., on a given leaf) more than once at successive intervals. The time intervals can depend on the experimental conditions and the target gene to be silenced. Two types of vectors (e.g. local and systemic) capable of inducing two different genes can be mixed and applied at a given location or more than one location.

Accordingly, in one aspect of the invention, a method for interfering with expression of selected gene(s) in plant cells through RNA silencing initiated by a recombinant viral vector which is incapable of systemic movement in the host plant is provided. The viral vector with a nucleic acid segment of the selected gene is designed such that, upon infection, it is capable of directing self-replication and producing a transcription product of the nucleic acid segment in the infected cells. The nucleic acid segment can be expressed from subgenomic promoter of the plant virus coat protein gene or movement protein gene and is expressed as part of messenger RNA (mRNA) of the coat protein gene or movement protein gene. Alternatively, the nucleic acid segment can be expressed from a synthetic subgenomic promoter and the nucleic acid segment is expressed independently of the mRNA of the coat protein gene or movement protein gene.

In another aspect of the invention, a method for interfering with expression of more than one gene in plant cells is provided: For example, two different types of vectors where each type is able to silence a gene different from the other vector is provided. The first type of recombinant viral vector (e.g. TMV) carrying a nucleic acid segment of a first gene and a second type of recombinant viral vector (e.g. TMV) carrying a nucleic acid segment of a second gene is used. Heterologous vectors for silencing two different genes can also be used. For example, the first recombinant viral vector having a recombinant genomic component of a first class of plant virus (e.g. mono-partite virus such as TMV) and second recombinant viral vector having a recombinant genomic component of a second class of plant virus (e.g. tri-partite virus such as AlMV) can be used. At least one of the classes of vectors can be systemic or both can be systemic.

In the methods of the present invention, chimeric viral vectors are also contemplated. For example, coat protein nucleic acid sequence of TMV can be inactivated and a heterologous coat protein nucleic acid sequence (e.g., AlMV) can be inserted. The heterologous coat protein nucleic acid sequence can be tailored so that the vector is either capable of systemic movement or remains locally. The systemic spread function in such a chimeric vector is conferred by the heterologous coat protein sequence. FIG. 3C shows a schematic of TMV chimeric vector. The chimeric viral vectors have been used by skilled artisan in the context of polypeptide production in plants.

The present invention is also directed to compositions and recombinant in vitro transcripts which are capable of inducing RNA silencing in a suitable host plant. Accordingly, in accordance with the subject invention, methods and compositions are provided for a novel methods of interfering with expression of genes in plants.

The practice of the present invention employs, unless otherwise indicated, conventional techniques of molecular biology, microbiology, virology, recombinant DNA technology, and immunology particularly, which are within the skill of the art. The recombinant plant viral nucleic acids for practicing the present invention can be constructed using techniques well known in the art. Briefly, manipulations, such as restriction, filling in overhangs to provide blunt ends, ligation of linkers, or the like, complementary ends of the fragments can be provided for joining and ligation. In carrying out the various steps, cloning is employed, so as to make the desired virus genomic component and heterologous nucleic acid combinations, to amplify the amount of DNA and to, allow for analyzing the DNA to ensure that the operations have occurred in proper manner. A wide variety of cloning vectors are available, where the cloning vector includes a replication system functional in *E. coli* and a marker which allows for selection of the transformed cells. Illustrative vectors include pBR332, pUC series, M13 mp series, pACYC184, etc for manipulation of the primary DNA constructs. See Life Technologies Catalogue (1999); Amersham Pharmacia Biotech Catalogue (1999). Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids. Suitable techniques have been described in standard references and well known to one skilled in the art. DNA manipulations and enzyme treatments are carried out in accordance with manufacturers' recommended procedures.

A variety of techniques are available for the genetic transformation of plants and plant tissues (i.e., the stable integration of foreign DNA into plants) and are well-known to those skilled in the art. These include transformation by *Agrobacterium* species and transformation by direct gene transfer. For example, the chimeric DNA constructs may be introduced into host cells obtained from dicotyledonous plants, such as tobacco and brassicas using standard *Agrobacterium* vectors by a transformation protocol such as that described by Moloney et al., 1989, Plant Cell Rep., 8:238–242 of Hinchee et al., 1988, Bio/Technol., 6:915–922; or other techniques known to those skilled in the art. For example, the use of T-DNA for transformation of plant cells has received extensive study and is amply described in Knauf, et al., (1983), Genetic Analysis of Host Range Expression by *Agrobacterium*, p. 245, In: Molecular Genetics of the Bacteria-Plant Interaction, Puhler, A. ed., Springer-Verlag, N.Y.; Hoekema et al., (1985), Chapter V, In: The Binary Plant Vector System Offset-drukkerij Kanters B. V., Alblasserdam; and An et al., (1985), EMBO J., 4:277–284. Briefly, explants can be co-cultivated with *A. tumefaciens* or *A. rhizogenes* to allow for transfer of the transcription construct to the plant cells. Following transformation using *Agrobacterium,* the plant cells are dispersed in an appropriate medium for selection, subsequently callus, shoots and eventually plantlets are recovered. The *Agrobacterium* host will harbour a plasmid comprising the vir genes necessary for transfer of the T-DNA to the plant cells. See also, Dodds, J. ed., Plant Genetic Engineering, Cambridge University Press, Cambridge (1985).

The use of non-*Agrobacterium* techniques permits the use of the constructs described herein to obtain transformation and expression in a wide variety of monocotyledonous and dicotyledonous plants and other organisms. These techniques are especially useful for species that are intractable in an *Agrobacterium* transformation system. Other techniques for gene transfer include biolistics (Sanford, 1988, Trends in Biotech., 6:299–302), electroporation (Fromm et al., 1985, Proc. Natl. Acad. Sci. U.S.A., 82:5824–5828; Riggs and Bates, 1986, Proc. Natl. Acad. Sci. U.S.A. 82:5602–5606 or PEG-mediated DNA uptake (Potrykus et al., 1985, Mol. Gen. Genet., 199:169–177).

In accordance with the present invention, the host plants included within the scope of the present invention are all species of higher and lower plants of the Plant Kingdom. Mature plants, seedlings, and seeds are included in the scope of the invention. A mature plant includes a plant at any stage in development beyond the seedling. A seedling is a very young, immature plant in the early stages of development. Specifically, plants that can be used as hosts to produce foreign sequences and polypeptides include and are not limited to Angiosperms, Bryophytes such as Hepaticae (liverworts) and Musci (mosses); Pteridophytes such as ferns, horsetails, and lycopods; Gymnosperms such as conifers, cycads, Ginkgo, and Gnetales; and Algae including Chlorophyceae, Phaeophpyceae, Rhodophyceae, Myxophyceae, Xanthophyceae, and Euglenophyceae.

Host plants used for gene silencing can be grown either in vivo and/or in vitro depending on the type of the selected plant and the geographic location. It is important that the selected plant is amenable to cultivation under the appropriate field conditions and/or in vitro conditions. The conditions for the growth of the plants are described in various basic books on botany, Agronomy, Taxonomy and Plant Tissue Culture, and are known to a skilled artisan in these fields.

Among angiosperms, the use of crop and/or crop-related members of the families are particularly contemplated. The plant members used in the present methods also include interspecific and/or intergeneric hybrids, mutagenized and/ or genetically engineered plants. These families include and not limited to Leguminosae (Fabaceae) including pea, alfalfa, and soybean; Gramineae (Poaceae) including rice, corn, wheat; Solanaceae particularly of the genus *Lycopersicon*, particularly the species *esculentum* (tomato), the genus *Solanum*, particularly the species *tuberosum* (potato) and *melongena* (eggplant), the genus *Capsicum*, particularly the species *annum* (pepper), tobacco, and the like; Umbelliferae, particularly of the genera *Daucus*, particularly the species *carota* (carrot) and *Apium*, particularly the species *graveolens dulce*, (celery) and the like; *Rutaceae*, particularly of the genera *Citrus* (oranges) and the like; Compositae, particularly the genus *Lactuca*, and the species *sativa* (lettuce), and the like and the Family Cruciferae, particularly of the genera *Brassica* and *Sinapis*. Examples of "vegetative" crop members of the family Brassicaceae include, but are not limited to, digenomic tetraploids such as *Brassica juncea* (L.) Czern. (mustard), *B. carinata* Braun (ethopian mustard), and monogenomic diploids such as *B. oleracea* (L.) (cole crops), *B. nigra* (L.) Koch (black mustard), *B. campestris* (L.) (turnip rape) and *Raphanus sativus* (L.) (radish). Examples of "oil-seed" crop members of the family Brassicaceae include, but are not limited to, *B. napus* (L.) (rapeseed), *B. campestris* (L.), *B. juncea* (L.) Czern. and *B. tournifortii* and *Sinapis alba* (L.) (white mustard). Flax plants are also contemplated.

Particularly preferred host plants are those that can be infected by AlMV. For example, it is known in the art that alfalfa mosaic virus has full host range. Other species that are known to be susceptible to the virus are: *Abelmoschus esculentus, Ageratum conyzoides, Amaranthus caudatus, Amaranthus retroflexus, Antirrhinum majus, Apium graveolens, Apium graveolens* var. *rapaceum, Arachis hypogaea, Astragalus glycyphyllos, Beta vulgaris, Brassica campestris* ssp. *rapa, Calendula officinalis, Capsicum annuum, Capsicum frutescens, Caryopteris incana, Catharanthus roseus,*

*Celosia argentea, Cheiranthus cheiri, Chenopodium album, Chenopodium amaranticol, Chenopodium murale, Chenopodium quinoa, Cicer arietinum, Cichium endiva, Ciandrum sativum, Crotalaria spectabilis, Cucumis melo, Cucumis sativus, Cucurbita pepo, Cyamopsis tetragonoloba, Daucus carota* (var. *sativa*), *Dianthus barbatus, Dianthus caryophyllus, Emilia sagittata, Fagopyrum esculentum, Glycine max, Gomphrena globosa, Helianthus annuus, Lablab purpureus, Lactuca sativa, Lathyrus odatus, Lens culinaris, Linum usitatissimum, Lupinus albus, Lycopersicon esculentum, Macroptilium lathyroides, Malva parvifla, Matthiola incana, Medicago hispida, Medicago sativa, Melilotus albus, Nicotiana bigelovii, Nicotiana clevelandii, Nicotiana debneyi, Nicotiana glutinosa, Nicotiana megalosiphon, Nicotiana rustica, Nicotiana sylvestris, Nicotiana tabacum, Ocimum basilicum, Petunia×hybrida, Phaseolus lunatus, Phaseolus vulgaris, Philadelphus, Physalis flidana, Physalis peruviana, Phytolacca americana, Pisum sativum, Solanum demissum, Solanum melongena, Solanum nigrum, Solanum nodiflum, Solanum rostratum, Solanum tuberosum, Sonchus oleraceus, Spinacia oleracea, Stellaria media, Tetragonia tetragonioides, Trifolium dubium, Trifolium hybridum, Trifolium incarnatum, Trifolium pratense, Trifolium repens, Trifolium subterraneum, Tropaeolum majus, Viburnum opulus, Vicia faba, Vigna radiata, Vigna unguiculata, Vigna unguiculata* ssp. *sesquipedalis*, and *Zinnia elegans*.

The following examples further illustrate the present invention, but of course, should not be construed as in any way limiting its scope. The examples below are carried out using standard techniques, that are well known and routine to those of skill in the art, except where otherwise described in detail.

EXAMPLE 1

Figure 5:
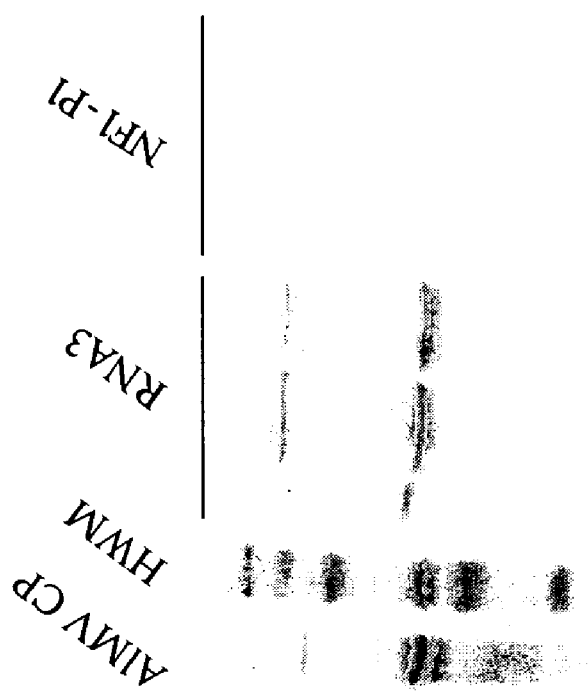

RNA-Triggered Gene Silencing of AlMV Replicase Gene (P1) in Transgenic P12 Plants For VIGS of AlMV replicase gene (P1) in transgenic P12 plants, a 100 nucleotide segment responsible for encoding C-terminus of AlMV P1 protein (RNA1) was engineered into genomic RNA3 of AlMV under the control of subgenomic promoter for RNA4. The recombinant viral construct (NF1-P1) was used to inoculate transgenic *Nicotiana tabacum* (*N. tabacum*) cv. Samsun NN plants expressing the AlMV P1 and P2 (P12) replicase genes. For inoculation, a mixture (RNA4:RNA3, 1:1,000) of in vitro transcription products diluted 1:2 in FES buffer was applied to the leaves of the transgenic P12 plants after abrading the leaf surface with carborundum (320-grit; Fisher, Pittsburgh, Pa.), and gently rubbed on the leaf surface to spread the inoculum and further abrade the surface. At 14 days post-inoculation, leaf samples were assessed for the presence of AlMV CP by immunoblot. Shown in FIG. 5 is Western blot analysis of CP in plants infected with wt AlMV or NF1-P1. Proteins were separated electrophoretically on a 12% SDS-polyacrylamide gel, transferred to a membrane, and reacted with different antibodies. Monoclonal antibodies specific for AlMV CP recognized 24.0 kDa protein only in extracts from wt-RNA3 infected plants. As FIG. 5 shows, AlMV CP could be detected only in plants inoculated with wild type RNA3 but not in samples from plants inoculated with recombinant RNA3 containing sequences from RNA1 of AlMV. These results show that RNA1 transgene was silenced resulting in the inhibition of AlMV RNA.

EXAMPLE 2

RNA-Triggered Gene Silencing of Ribulose Bisphosphate Carboxylase (Rubisco) in *Medicago truncatula* and *N. benthamiana* Plants Plants were inoculated with w/t AlMV (c+) or recombinant virus (bis) containing fragment from Ribulose bisphosphate carboxylase small chain precursor. 7 dpi accumulation of virus in cotyledons of bis is as expected and comparable to that of c+. After 14 dpi, however, accumulation of AlMV CP in bis is significantly decreased compared to that of c+. This is similar to the picture observed during infection with virus containing chalconesynthase gene. This kind of decrease in virus accumulation is not observed during w/t AlMV infection. Thus, the decrease in AlMV accumulation could be the result of gene silencing.

The results are illustrated in FIGS. 6 and 7. In FIG. 6, the accumulation of AlMV coat protein in different organs of a host plant after inoculation with the viral vector capable of systemic spread is shown. More specifically, the illustration shows western analysis of alfalfa mosaic virus coat protein accumulation in cotyledons (cot), leaves (l) and roots (r) of *Medicago truncatula* 10 dpi (days post inoculation). Presented in FIG. 7 is western analysis of alfalfa mosaic virus showing coat protein accumulation in cotyledons (7 dpi) and systemically infected leaves (14 dpi) of *Medicago truncatula*. Note that, by 14 dpi, the AlMV coat protein accumulation significantly decreased.

EXAMPLE 3

RNA-Triggered Gene Silencing of Beta-Amyrin Synthase (bAS) Gene in *Medicago truncatula* Plants To demonstrate silencing of beta-amyrin synthase gene in *Medicago truncatula* plants, these plants were infected with an AlMV vector containing a nucleic acid segment for beta-amyrin synthase gene of *Medicago*. Western analysis of the plants 5 dpi showed significant accumulation of CP locally in the plants. Western analysis after 14 dpi showed significant decrease or absence of CP in infected plants. Leaf samples from plants infected with wild type AlMV (positive control) and plants infected with the recombinant AlMV viral vector with beta-amyrin synthase fragment, and healthy plants were used for Western analysis. Data not presented herein.

All publications and references, including but not limited to patents, cited in this specification, are herein incorporated by reference in their entirety as if each individual publication or reference were specifically and individually indicated to be incorporated by reference herein as being fully set forth. While this invention has been described with a reference to specific embodiments, it will be obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

TABLE 1

Sequences of Genes Fragments And PCR Primers

A. Chalcone Synthase (ChS) Minus strand (template)

5'CGA TTA AGT GAG TAA TCT TTG ACT TTG GTT GAC CCC ATT CTT TTA (SEQ ID NO: 1)

TAG CCT TCA CTG CAG CCT CCT TCC CTA GTC TAG GTA CCT CTA CCA

CCA CCA TGT CTT GCC TAG CAT CCA ATG AAG GGG CCA TGT ATT CAC

AAA CAC TAG3'

5'primer (ChS5')
5'GCG CTC GAG CGA TTA AGT GAG TAA TCT TTG ACT TTG GTT GAC CCC (SEQ ID NO: 2)
ATT CTT TTA TAG CCT TCA CTG CAG CCT CCT TCC CTA GTC TAG GTA3'

3'primer (ChS3')
5'GC GTC GAC AT CTA GTG TTT GTG AAT ACA TGG CCC CTT CAT GGG ATG (SEQ ID NO: 3)
CTA GGC AAG ACA TGG TGG TGG TAG AGG TAC CTA GAC TAG GGA3'

B. Beta-amyrin synthase (BAS) Minus strand (TEMPLATE)

5'GAG CAG GCC AAT GGC CAT CAC TGG TTT GCA ATG CTG CTA GAT GGT (SEQ ID NO: 4)

GTG TGC CCC TTC TCA ACG TTG TCG TTG CTT TCT CAT ATG TTA TCT CTT

CTC CAT CTT CTA TCT TCA CTC CAT CTA TTG TTT GCA TAA AGT TAT

TTT CTC3'

5'primer (BAS5')
5'GCG CTC GAG GAG CAG GCC AAT GGC CAT CAC TGG TTT GCA ATG CTG (SEQ ID NO: 5)
CTA GAT GGT GTG TGC CCC TTC TCA ACG TTG TCG TTG CTT TCT CAT3'

3'primer (BAS3')
5'GC GTC GAC AT GAG AAA ATA ACT TTA TGC AAA CAA TAG ATG GAG TGA (SEQ ID NO: 6)
AGA TAG AAG ATG GAG AAG AGA TAA CAT ATG AGA AAG CAA CGA3'

C. Ribulose bisphosphate carboxylase (Rubisco) Minus strand (TEMPLATE)

5'TGC TGG TGT GTG AGC AAT GAA ACT AAT GCA CTG CAC TTG ACG AAC ATT GTC (SEQ ID NO: 7)

AAA TCC AAT GAT TCT GAT GAA TGA TTC TGG GTA AGC AGC TTT AGC TTC AGC AAG CTC

CTT CAA CAC TTG AGA AGA ATC AGT GGC TCC3'

5'primer (Rubisco)
5'GCG CTC GAG TGC TGG TGT GTG AGC AAT GAA ACT AAT GCA CTG CAC TTG ACG (SEQ ID NO: 8)
AAC ATT GTC AAA TCC AAT GAT TCT GAT GAA TGA TTC3'

3'primer (Rubisco)
5'GC GTC GAC AT GGA GCC ACT GAT TCT TCT CAA GTG TTG AAG GAG CTT GCT GAA (SEQ ID NO: 9)
GCT AAA GCT3'

What is claimed is:

1. A method for interfering with the expression of a selected gene in plant cells through RNA-triggered gene silencing initiated by a recombinant viral vector, the method comprising:
   (a) infecting said cells at one or more locations of a host plant with the recombinant viral vector, said viral vector comprising a recombinant genomic component of a plant virus and a nucleic acid segment of the selected gene, wherein said vector, upon infection, directs self-replication and produces a transcription product of the nucleic acid segment in said cells but is incapable of systemic movement in the host plant, wherein the nucleic acid segment is expressed from a subgenomic promoter of the plant virus coat protein gene or movement protein gene and is expressed as part of messenger RNA (mRNA) of the coat protein gene or movement protein gene; and
   (b) growing the host plant, wherein the transcription product interferes with the expression of the selected gene in said as determined by a genetic, biochemical or phenotypic change attributable to said interference.

2. The method of claim 1, wherein the selected gene is native to the host plant.

3. The method of claim 2, wherein the selected gene is a lignin specific gene, phloem specific gene, a flavonoid pathway gene, a receptor gene, a hormonal gene, a gene specific to fruit maturation, a gene specific to seed maturation, a gene specific to seed germination, a gene responsible for enhanced root formation, a gene responsible for tissue regeneration in vitro, a gene responsible for transport protein, a gene responsible for signal transduction, a crown gall gene, beta-amyrin synthase gene, Rubisco gene or chalcone synthase gene.

4. The method of claim 1, wherein the selected gene is a transgene in the host plant.

5. The method of claim 4, wherein the transgene is the plant virus replicase gene or a crown gall gene.

6. The method of claim 4, wherein the transgene is native to a monocotyledonous or dicotyledonous plant.

7. The method of claim 1, wherein the virus is a monopartite virus.

8. The method of claim 7, wherein the virus is a tobamo virus.

9. The method of claim 1, wherein the virus is a tri-partite virus.

10. The method of claim 9, wherein the virus is AlMV, an ilarvirus or a cucumber mosaic virus.

11. The method of claim 1, wherein the nucleic acid segment does not naturally occur in the genome of the plant virus.

12. The method of claim 11, wherein the nucleic acid segment is between 20 to 300 nucleotides long.

13. The method of claim 11, wherein the nucleic and segment consists of up to 200 nucleotides.

14. A method for interfering with the expression of a selected gene in plant cells through RNA-triggered gene silencing, the method comprising:
   (a) infecting said cells at one or more locations of a host plant with a recombinant viral vector which is an initiator of the RNA-triggered gene silencing in said cells, said vector comprising a recombinant genomic component of an alfalfa mosaic virus and a nucleic acid segment of the selected gene,
   wherein said vector, upon infection, directs self-replication and produces a transcription product of the nucleic acid segment in said cells, wherein the nucleic acid segment is expressed from a subgenomic promoter of the alfalfa mosaic virus coat protein gene or movement protein gene and is expressed as part of messenger RNA (mRNA) of the coat protein gene or movement protein gene; and
   (b) growing the host plant, wherein the transcription product interferes with the expression of the selected gene in said cells as determined by a genetic, biochemical or phenotypic change attributable to said interference.

15. A method for interfering with the expression of a selected gene in plant cells and accumulation of a recombinant viral vector in said cells through RNA-triggered gene silencing, the method comprising:
   (a) infecting said cells of a host plant at one or more locations with the recombinant viral vector which is both an initiator and a target of the RNA-triggered gene silencing in the host plant, said viral vector comprising a recombinant genomic component of a plant virus and a nucleic acid segment of the selected gene, wherein said viral vector, upon infection, directs self-replication and produces a transcription product of the nucleic acid segment at said locations but is incapable of systemic movement in the host plant, wherein the nucleic acid segment is expressed from a subgenomic promoter of the plant virus coat protein gene or movement protein gene and is expressed as part of messenger RNA (mRNA) of the coat protein gene or movement protein gene; and
   (b) growing the host plant, wherein the transcription product interferes with the expression of the selected gene in said cells as determined by a genetic, biochemical or phenotypic change attributable to said interference, and the accumulation of the recombinant viral vector.

16. A method for interfering with the expression of selected genes in plant cells of a host plant through recombinant viral vector initiated RNA-triggered gene silencing, the method comprising:
   (a) infecting said cells at one or more locations of the host plant with at least two types of recombinant viral vectors such that each of said vectors, upon infection, directs self-replication and produces a transcription product of a nucleic acid segment present in each of said vectors at said locations, which nucleic acid segment is also found in one of the plant expressed genes, wherein the nucleic acid segment is expressed from a subgenomic promoter of the plant virus coat protein gene or movement protein gene and is expressed as part of messenger RNA (mRNA) of the coat protein gene or movement protein gene,
      wherein a first type of recombinant viral vector comprises a recombinant genomic component of a plant virus, and a nucleic acid segment of a first gene,
      wherein a second type of recombinant viral vector comprises the recombinant genomic component of the plant virus, and a nucleic acid segment of a second gene,
      wherein said vectors are both initiators and targets of the RNA-triggered gene silencing in the host plant; and
   (b) growing the host plant, wherein the transcription product interferes with the expression of the selected gene in said cells as determined by a genetic, biochemical or phenotypic change attributable to said interference.

17. The method of claim 16, wherein said vectors are so constructed that said vectors are capable of limited cell-to-cell movement but incapable of systemic movement in the host plant.

18. The method of claim 16, wherein the first and second vectors are administered either simultaneously or sequentially at the same location or at different locations of the host plant.

19. A method for interfering with the expression of selected genes in plant cells of a host plant through recombinant viral vector initiated RNA-triggered gene silencing, the method comprising:
 (a) infecting the host plant at one or more locations with a first recombinant viral vector and a second recombinant viral vector so that each of said vectors, upon infection, directs self-replication and produces a transcription product of a nucleic acid segment present in each of said vectors at said locations, which nucleic acid segment is also found in one of the plant expressed genes,
  wherein the first recombinant viral vector comprises a recombinant genomic component of a first class of plant virus and a nucleic acid segment of a first gene such that the nucleic acid segment of the first gene is expressed from subgenomic promoter of the first class of plant virus coat protein gene or movement protein gene and is expressed as part of messenger RNA (mRNA) of the coat protein gene or movement protein gene of the first class of virus,
  wherein the second recombinant viral vector comprises a recombinant genomic component of a second class of plant virus and a nucleic acid segment of a second gene such that the nucleic acid segment of the second gene is expressed from a subgenomic promoter of the second class of plant virus coat protein gene or movement protein gene and is expressed as part of messenger RNA (mRNA) of the coat protein gene or movement protein gene of the second class of virus,
  wherein said vectors are both initiators and targets of the RNA-triggered gene silencing in the host plant; and
 (b) growing the host plant, wherein the transcription product interferes with the expression of each of said genes in said cells determined by a genetic, biochemical or phenotypic change attributable to said interference.

20. The method of claim 19, wherein the first and second vectors are administered either simultaneously or sequentially at the same location or at different locations of the host plant.

21. A method for interfering with the expression of selected genes in plant cells through recombinant viral vector initiated RNA-triggered gene silencing, the method comprising:
 (a) infecting said cells at one or more locations of a host plant with
  a first recombinant viral vector, said first vector comprising a recombinant genomic component of a first class of plant virus and a nucleic acid segment of a first gene such that the nucleic acid segment of the first gene is expressed from a subgenomic promoter of the first class of plant virus coat protein gene or movement protein gene and is expressed as part of messenger RNA (mRNA) of the coat protein gene or movement protein gene of the first class of virus, and
  a second recombinant viral vector, said second vector comprising a recombinant genomic component of a second class of plant virus and a nucleic acid segment of a second gene such that the nucleic acid segment of the second gene is expressed from a subgenomic promoter of the second class of plant virus coat protein gene or movement protein gene and is expressed as part of messenger RNA (mRNA) of the coat protein gene or movement protein gene of the second class of virus,
  wherein said vectors are both initiators and targets of the RNA-triggered gene silencing in the host plant,
  wherein each of said vectors, upon infection, is capable of directing self-replication and producing a transcription product of the nucleic acid segment present in each of said vectors, and
  wherein at least one of said vectors is capable of systemic movement in the host plant; and
 (b) growing the host plant, wherein the transcription product interferes with the expression of each of said genes in said cells as determined by a genetic, biochemical or phenotypic change attributable to said interference.

22. The method of claim 21, wherein the first and second vectors are administered either simultaneously or sequentially at the same location or at different locations of the host plant.

23. A method for interfering with the expression of a selected gene in plant cells through RNA-triggered gene silencing, the method comprising:
 (a) infecting said cells at one or more locations of a host plant with a recombinant viral vector, said vector comprising a recombinant genomic component of AlMV and a nucleic acid segment of the selected gene,
  wherein said vector, upon infection, directs self-replication and produces a transcription product of the nucleic acid segment,
  wherein the nucleic acid segment is expressed from a subgenomic promoter of the AlMV coat protein gene or movement protein gene and is expressed as part of messenger RNA (mRNA) of the coat protein gene or movement protein gene, and
  wherein said vector is both an initiator and a target of the RNA-triggered gene silencing in said cells; and
 (b) growing the host plant, wherein the transcription product interferes with the expression of the selected gene in said cells as determined by a genetic, biochemical or phenotypic change attributable to said interference.

24. The method of claim 23, wherein the recombinant genomic component of AlMV comprises replicase nucleic acids, a movement protein encoding nucleic acid sequence and a coat protein encoding nucleic acid sequence lacking one or more nucleotides sufficient to prevent translation of coat protein.

25. A method for interfering with the expression of selected genes in plant cells through RNA-triggered gene silencing, the method comprising:
 (a) infecting said cells at one or more locations of a host plant with a recombinant viral vector, said vector comprising:
  a recombinant genomic component of a plant virus;
  a nucleic acid segment of a first gene placed immediately upstream of movement protein nucleic acid sequence in said genomic component of said plant virus and under control of a subgenomic promoter also controlling the movement protein sequence;

a nucleic acid segment of a second gene placed immediately upstream of coat protein nucleic acid sequence in said genomic component of the plant virus and under control of a subgenomic promoter also controlling the coat protein sequence, wherein said vector, upon infection, directs self-replication and produces a transcription product of said nucleic acid segments; and wherein said vector is both an initiator and a target of the RNA-triggered gene silencing in said cells, and (b) growing the host plant, wherein the transcription product interferes with the expression of the first or the second gene in said cells as determined by a genetic, biochemical or phenotypic change attributable to said interference.

26. The method of claim 25, wherein the plant virus is TMV or AlMV.

27. The method of claim 14, wherein said alfalfa mosaic virus vector is both an initiator and a target of the RNA-triggered gene silencing in said cells.

* * * * *

SEQUENCE LISTING

<160> NUMBER OF SEQ ID NOS: 11

<210> SEQ ID NO 1
<211> LENGTH: 144
<212> TYPE: DNA
<213> ORGANISM: Artificial Sequence
<220> FEATURE:
<223> OTHER INFORMATION: Chalcone Synthase Minus Strand (Template)

-continued

```
<400> SEQUENCE: 1
cgattaagtg agtaatcttt gactttggtt gaccccattc ttttatagcc ttcactgcag      60
cctccttccc tagtctaggt acctctacca ccaccatgtc ttgcctagca tccaatgaag     120
gggccatgta ttcacaaaca ctag                                           144

<210> SEQ ID NO 2
<211> LENGTH: 90
<212> TYPE: DNA
<213> ORGANISM: Artificial Sequence
<220> FEATURE:
<223> OTHER INFORMATION: Primer

<400> SEQUENCE: 2
gcgctcgagc gattaagtga gtaatctttg actttggttg accccattct tttatagcct     60
tcactgcagc ctccttccct agtctaggta                                      90

<210> SEQ ID NO 3
<211> LENGTH: 88
<212> TYPE: DNA
<213> ORGANISM: Artificial Sequence
<220> FEATURE:
<223> OTHER INFORMATION: Primer

<400> SEQUENCE: 3
gcgtcgacat ctagtgtttg tgaatacatg gccccttcat tggatgctag gcaagacatg     60
gtggtggtag aggtacctag actaggga                                        88

<210> SEQ ID NO 4
<211> LENGTH: 144
<212> TYPE: DNA
<213> ORGANISM: Artificial Sequence
<220> FEATURE:
<223> OTHER INFORMATION: Beta-amyrin Synthase Minus Strand (Template)

<400> SEQUENCE: 4
gagcaggcca atggccatca ctggtttgca atgctgctag atggtgtgtg ccccttctca     60
acgttgtcgt tgctttctca tatgttatct cttctccatc ttctatcttc actccatcta   120
ttgtttgcat aaagttattt tctc                                           144

<210> SEQ ID NO 5
<211> LENGTH: 90
<212> TYPE: DNA
<213> ORGANISM: Artificial Sequence
<220> FEATURE:
<223> OTHER INFORMATION: Primer

<400> SEQUENCE: 5
gcgctcgagg agcaggccaa tggccatcac tggtttgcaa tgctgctaga tggtgtgtgc     60
cccttctcaa cgttgtcgtt gctttctcat                                      90

<210> SEQ ID NO 6
<211> LENGTH: 88
<212> TYPE: DNA
<213> ORGANISM: Artificial Sequence
<220> FEATURE:
<223> OTHER INFORMATION: Primer

<400> SEQUENCE: 6
gcgtcgacat gagaaaataa ctttatgcaa acaatagatg gagtgaagat agaagatgga     60
```

```
gaagagataa catatgagaa agcaacga                                          88
```

<210> SEQ ID NO 7
<211> LENGTH: 138
<212> TYPE: DNA
<213> ORGANISM: Artificial Sequence
<220> FEATURE:
<223> OTHER INFORMATION: Rubisco Minus Strand (Template)

<400> SEQUENCE: 7

```
tgctggtgtg tgagcaatga aactaatgca ctgcacttga cgaacattgt caaatccaat       60
gattctgatg aatgattctg ggtaagcagc tttagcttca gcaagctcct tcaacacttg      120
agaagaatca gtggctcc                                                   138
```

<210> SEQ ID NO 8
<211> LENGTH: 87
<212> TYPE: DNA
<213> ORGANISM: Artificial Sequence
<220> FEATURE:
<223> OTHER INFORMATION: Primer

<400> SEQUENCE: 8

```
gcgctcgagt gctggtgtgt gagcaatgaa actaatgcac tgcacttgac gaacattgtc       60
aaatccaatg attctgatga atgattc                                          87
```

<210> SEQ ID NO 9
<211> LENGTH: 61
<212> TYPE: DNA
<213> ORGANISM: Artificial Sequence
<220> FEATURE:
<223> OTHER INFORMATION: Primer

<400> SEQUENCE: 9

```
gcgtcgacat ggagccactg attcttctca agtgttgaag gagcttgctg aagctaaagc       60
t                                                                      61
```

<210> SEQ ID NO 10
<211> LENGTH: 138
<212> TYPE: DNA
<213> ORGANISM: Artificial Sequence
<220> FEATURE:
<223> OTHER INFORMATION: Rubisco Gene Fragment

<400> SEQUENCE: 10

```
tgctggtgtg tgagcaatga aactaatgca ctgcacttga cgaacattgt caaatccaat       60
gattctgatg aatgattctg ggtaagcagc tttagcttca gcaagctcct tcaacacttg      120
agaagaatca gtggctcc                                                   138
```

<210> SEQ ID NO 11
<211> LENGTH: 144
<212> TYPE: DNA
<213> ORGANISM: Artificial Sequence
<220> FEATURE:
<223> OTHER INFORMATION: Beta-amyrin Synthase Gene Fragment

<400> SEQUENCE: 11

```
gagcaggcca atggccatca ctggtttgca atgctgctag atggtgtgtg cccttctca       60
acgttgtcgt tgctttctca tatgttatct cttctccatc ttctatcttc actccatcta    120
ttgtttgcat aaagttattt tctc                                           144
```